United States Patent
Olivieri et al.

(10) Patent No.: US 9,687,789 B2
(45) Date of Patent: Jun. 27, 2017

(54) ULTRAFILTRATION FOR PREPARING OUTER MEMBRANE VESICLES

(75) Inventors: Roberto Olivieri, Siena (IT); Fabio Sabbatini, Siena (IT); Ilio Marsili, Siena (IT)

(73) Assignee: GLAXOSMITHKLINE BIOLOGICALS SA, Rixensart (BE)

(*) Notice: Subject to any disclaimer, the term of this patent is extended or adjusted under 35 U.S.C. 154(b) by 2368 days.

(21) Appl. No.: 10/564,474

(22) PCT Filed: Jul. 15, 2004

(86) PCT No.: PCT/IB2004/002475
§ 371 (c)(1),
(2), (4) Date: Nov. 20, 2006

(87) PCT Pub. No.: WO2005/004908
PCT Pub. Date: Jan. 20, 2005

(65) Prior Publication Data
US 2007/0087017 A1   Apr. 19, 2007

(30) Foreign Application Priority Data
Jul. 15, 2003 (GB) .................. 0316560.2

(51) Int. Cl.
| | |
|---|---|
| *C12N 1/00* | (2006.01) |
| *C12N 1/12* | (2006.01) |
| *C12N 1/02* | (2006.01) |
| *C12N 1/20* | (2006.01) |
| *A61K 39/095* | (2006.01) |
| *B01D 61/14* | (2006.01) |
| *B01D 61/16* | (2006.01) |
| *C12N 1/06* | (2006.01) |
| *C12R 1/36* | (2006.01) |
| *C07K 14/22* | (2006.01) |
| *C12R 1/01* | (2006.01) |
| *A61K 39/00* | (2006.01) |

(52) U.S. Cl.
CPC .......... *B01D 61/145* (2013.01); *A61K 39/095* (2013.01); *B01D 61/147* (2013.01); *B01D 61/16* (2013.01); *C12N 1/005* (2013.01); *C12N 1/06* (2013.01); *C12R 1/36* (2013.01); *A61K 2039/6018* (2013.01); *B01D 2311/04* (2013.01); *B01D 2311/16* (2013.01); *C07K 14/22* (2013.01); *C12N 1/00* (2013.01); *C12N 1/02* (2013.01); *C12N 1/20* (2013.01); *C12R 1/01* (2013.01)

(58) Field of Classification Search
CPC .............. A61K 2039/095; A61K 38/47; A61K 9/0048; C07K 2316/96; C12N 1/20; C12N 1/02; C12N 1/00; C12R 1/01
See application file for complete search history.

(56) References Cited

U.S. PATENT DOCUMENTS

| | | | |
|---|---|---|---|
| 5,597,572 A | 1/1997 | Huergo et al. | |
| 5,726,292 A | 3/1998 | Lowell | |
| 5,747,653 A * | 5/1998 | Huergo et al. ............. | 530/389.5 |
| 6,180,111 B1 | 1/2001 | Stein et al. | |
| 6,355,253 B1 | 3/2002 | Zlotnick | |
| 6,451,317 B1 | 9/2002 | Blake et al. | |
| 6,476,201 B1 | 11/2002 | Lowell et al. | |
| 6,558,677 B2 * | 5/2003 | Zollinger et al. .......... | 424/234.1 |
| 6,812,023 B1 * | 11/2004 | Lamparski ........... | C12N 5/0639 |
| | | | 435/325 |
| 6,936,261 B2 | 8/2005 | Granoff et al. | |
| 7,018,636 B1 | 3/2006 | Bhattacharjee et al. | |
| 7,384,645 B2 | 6/2008 | Foster et al. | |
| 7,628,995 B2 | 12/2009 | Bos et al. | |
| 7,754,218 B2 | 7/2010 | Contorni et al. | |
| 7,838,014 B2 | 11/2010 | Biemans et al. | |
| 8,007,815 B1 | 8/2011 | Granoff et al. | |
| 8,029,807 B2 | 10/2011 | Bos et al. | |
| 8,808,711 B2 | 8/2014 | Oster et al. | |
| RE45,137 E | 9/2014 | O'Hagan et al. | |
| 8,968,748 B2 | 3/2015 | Granoff et al. | |
| 2003/0059444 A1 | 3/2003 | Shoemaker et al. | |
| 2004/0241176 A1 * | 12/2004 | Lamparski ......... | A61K 39/0011 |
| | | | 424/185.1 |
| 2006/0029621 A1 * | 2/2006 | Granoff et al. ............ | 424/249.1 |
| 2006/0204520 A1 * | 9/2006 | Berthet et al. ............. | 424/200.1 |

(Continued)

FOREIGN PATENT DOCUMENTS

| | | | |
|---|---|---|---|
| EP | 0011243 B1 | 4/1982 | |
| EP | 1741443 B1 | 10/2007 | |

(Continued)

OTHER PUBLICATIONS

Fukasawa et al. (Vaccine, 1999; 17: 2951-2958).*
van Reis et al. (Current Opinion in Biotechnology, 2001; 12: 208-211).*
Dorward et al., Applied and Environmental Microbiology, 1990; 56(6): 1960-62.*
Tangential Flow Filtration; http://www.pall.com/main/Biopharmaceuticals/Tangential-Flow-Filtration-Introduction-51907.page; Oct. 7, 2011.*

(Continued)

*Primary Examiner* — Gary Nickol
*Assistant Examiner* — Lakia Tongue

(57) ABSTRACT

In place of a step of centrifugation during preparation of outer membrane vesicles (OMVs) from bacteria, the invention utilizes ultrafiltration. This allows much larger amounts of OMV-containing supernatant to be processed in a much shorter time. Thus the invention provides a process for preparing bacterial OMVs, comprising a step of ultrafiltration. The ultrafiltration step is performed on an aqueous suspension of OMVs after they have been prepared from bacteria and the OMVs remain in suspension after the filtration step. The invention is particularly useful for preparing OMVs from *Neisseria meningitidis*.

15 Claims, 2 Drawing Sheets

(56) References Cited

U.S. PATENT DOCUMENTS

| | | | |
|---|---|---|---|
| 2006/0240045 | A1 | 10/2006 | Berthet et al. |
| 2007/0059329 | A1 | 3/2007 | Norals et al. |
| 2011/0182942 | A1 | 7/2011 | Zollinger |
| 2011/0262484 | A1 | 10/2011 | Feavers |

FOREIGN PATENT DOCUMENTS

| | | |
|---|---|---|
| WO | WO-99/61053 | 12/1999 |
| WO | WO-01/34642 | 5/2001 |
| WO | WO-01/91788 A1 | 12/2001 |
| WO | WO-02/09643 | 2/2002 |
| WO | WO-02/062378 A2 | 8/2002 |
| WO | WO-2004/014417 A2 | 2/2004 |
| WO | WO-2004/019977 | 3/2004 |
| WO | WO-2004/054611 A1 | 7/2004 |
| WO | WO-2005/004908 | 1/2005 |
| WO | WO-2005/064021 A2 | 7/2005 |
| WO | WO-2006/046143 A2 | 5/2006 |
| WO | WO-2009/158142 A1 | 12/2009 |
| WO | WO-2010/109325 A2 | 9/2010 |

OTHER PUBLICATIONS

Frasch et al., Methods in Molecular Medicine, 2001; 66: 81-107.*
Sacchi et al., Journal; of Clinical Microbiology, 2001; 39(8): 2897-2903.*
O'Hallahan et al. (2009). "Delivering a safe and effective strain-specific vaccine to control an epidemic of group B meningococcal disease," *NZMJ* 122(1291):48-59.
Zollinger et al. (1979). "Complex of Meningococcal Group B Polysaccharide and Type 2 Outer Membrane Protein Immunogenic in Man," *J. Clin. Invest.* 63:836-848.
Arigita, C. at al. "Stability of mono- and trivalent meningococcal outer membrane vesicle vaccines," Vaccine, vol. 22, No. 5-0, 2004, pp. 630-643.
Bjune et al., "Effect of outer membrane vesicle vaccine against group B meningococcal disease in Norway," Lancet 338(8775):1093-1096,1991.
Boslego J, et al. (1995). Efficacy, safety, and immunogenicity of a meningococcal group B (15:P1.3) outer membrane protein vaccine in Iquique, Chile. Chilean National Committee for Meningococcal Disease. Vaccine 13:821-829.
Collins (2011). "Gram-negative outer membrane vesicles in vaccine development," Discov Med, 12(62):7-15.
Corbel, "Control testing of combined vaccines: a consideration of potential problems and approaches," Biologicals 22(4):353-360, 1994.
Dalseq et al. (May 14, 1999). "Outer membrane vesicles from group B meningococci are strongly immunogenic when given intranasally to mice" Vaccine 17(19):2336-2345.
De Kleijn, ED. et al. "Immunogenicity and safety of a hexavalent meningococcal outer membrane-vesicle vaccine in children of 2-3 and 7-8 years of age," Vaccine, 18:1456-1466(2000).
de Moraes JC, et al. (1992). Protective efficacy of a serogroup B meningococcal vaccine in Sao Paulo, Brazil. Lancet 340: 1074-1078.
Debbag et al., "Evaluation of Adverse Reactions Associated to Antimeningococcal BC Vaccination in 16,700 Children" Clinical Infectious Diseases, vol. 21, pp. 790-A420 (Sep. 1995).
Declaration from Christiane Feron, filed in opposition against EP1534326, dated Sep. 28, 2009, 3 pages.
Devoe et al. (1973). "Release of endotoxin in the form of cell wall blebs during in vitro growth of Neisseria meningitidis," J Exp Med, 138(5):1156-67.
Experimental data regarding OMV expression following OMV extraction, filed in opposition against EP1534326, dated Oct. 2, 2009, 1 page.
Experimental data: expression of NspA, '287' and '741' on 3 strains of bacteria, filed in opposition against EP1534326, dated Aug. 4, 2010. 2 pages.

Frasch et al. (2001). "Outer Membrane Protein Vesicle Vaccines for Meningococcal Disease," Chapter 7 in "Methods in Molecular Medicine, Meningococcal Vaccines: Methods and Protocols," Pollard et al. (Ed), Humana Press, Totowa, New Jersey, vol. 66, pp. 81-107.
Fredrikson et al. (1991). Production, characterization and control of MenB-vaccine "Folkehelsa": an outer membrane vesicle vaccine against group B meningococcal disease. NIPH Annals 14:67-79.
Fukasawa et al. (2004). "Adjuvant can improve protection induced by OMV vaccine against Neisseria meningitidis serogroups B/C in neonatal mice" FEMS Immunol. Med. Microbiol. 41:205-210.
Gao et al. (1996). "Study on the LOS Antigenicity of 2 Candidate Strains for Meningococcal Vaccine of Serogroup B," Zhonghua Weishengwuxue He Mianyixue Zazhi 16(6):405-408. (English language Abstract only).
Henry, et al.(2004). "Improved methods for producing outer membrane vesicles in Gram-negative bacteria," Research in Microbiology, 155:437-446.
Hoiby et al. (1991). "Bactericidal antibodies after vaccination with the Norwegian meningococcal serogroup B outer membrane vesicle vaccine: a brief survey," NIPH Annals 14(2):147-155.
Hoiby et al. (1991). "The Norwegian meningococcal serogroup B outer membrane vesicle vaccine protection trials: case tracing, meningococcal antigen detection and serological diagnosis," NIPH Annals, 14(2):107-123.
Hoist et al. (2003). "Serum bactericidal activity correlates with the vaccine efficacy of outer membrane vesicle vaccines against Neisseria meningitidis serogroup B disease," Vaccine 21(7-8):734-737.
Hoist et al. (2009). "Properties and clinical performance of vaccines containing outer membrane vesicles from Neisseria meningitidis," Vaccine; 27 Suppl 2:B3-12.
Interlocutory decision in opposition proceedings, filed in opposition against EP1534326, dated Mar. 25, 2010, 11 pages.
Katial et al. (2002). "Immunogenicity and Safety Testing of a Group B Intranasal Meningococcal Native Outer Membrane Vesicle Vaccine," Infection and Immunity 70(2):702-707.
Koeberling et al. (2007). "Improved immunogenicity of a H44/76 group B outer membrane vesicle vaccine with over-expressed genome-derived Neisserial antigen 1870," Vaccine 25(10):1912-1920.
List of Journals from SpringerProtocols website about Methods in Molecular Biology, filed in Opposition against EP1644035, dated Oct. 18, 2014, 5 pages.
Milagres L G et al. (Aug. 2000) "Bactericidal antibody response to Neisseria meningitidis serogroup B in patients with bacterial meningitis: effect of immunization with an outer membrane protein vaccine," FEMS Immunology and Medical Microbiology 28(4):319-327.
Norheim et al. (2004). "Immunogenicity and bactericidal activity in mice of an outer membrane protein vesicle vaccine against Neisseria meningitidis serogroup A disease," Vaccine, 22: 2171-2180.
Norheim et al. (2005). "Development and characterisation of outer membrane vesicle vaccines against serogroup A Neisseria meningitidis" Vaccine 23(29):3762-3774.
Notice of Appeal by Carpmaels & Ransford, filed in Opposition against EP1644035, dated Mar. 24, 2014, 1 page.
Notice of Appeal by GlaxoSmithKline Biologicals S.A., filed in relation to EP1534326, dated Jun. 3, 2010, 2 pages.
Notice of opposition by GlaxoSmithKline Biologicals S.A., filed in opposition against EP1534326, dated Mar. 3, 2008, 19 pages.
Notice of Opposition, filed in Opposition against EP1644035, dated May 24, 2012, 15 pages.
O'Hallahan J, et al. 2004. The strategy to control New Zealand's epidemic of Group B meningococcal disease. PIDJ 23: S293-S298.
Oster et al. (2007). "Immunogenicity and safety of a strain-specific MenB OMV vaccine delivered to under 5-year olds in New Zealand," Vaccine, 25:3075-9.
Parkhill et al. (2000). "Complete DNA Sequence of a Serogroup A Strain of Neisseria meningitides Z2491," Nature, 404(6777):502-506.
Patentee's response to Notice of Opposition, filed in Opposition against EP1644035, dated Mar. 12, 2013, 9 pages.

(56) References Cited

OTHER PUBLICATIONS

Patentee's response to opposition, filed in opposition against EP1534326, dated Jan. 19, 2009, 11 pages.
Peeters et al. (1996). "Phase I clinical trial with a hexavalent PorA containing meningococcal outer membrane vesicle vaccine," Vaccine 14(10):1009-1015.
Perkins et al. (1998). "Immunogenicity of two efficacious outer membrane protein-based serogroup B meningococcal vaccines among young adults in Iceland," The Journal of Infectious Disease 177:683-691.
Reply to Statement of Grounds of Appeal by Nederlandsch Octrooibureau, filed in Opposition against EP1644035, dated Oct. 15, 2014, 8 pages.
Rosenqvist et al. (1995). "Human Antibody Response to Meningococcal Outer Membrane Antigens after Three Doses of the Norwegian Group B Meningococcal Vaccine," Infection and Immunity 63(12):4642-4652.
Rosenqvist et al., "Effect of Aluminum Hydroxide and Meningococcal Serogroup C Capsular Polysaccharide on the Immunogenicity and Reactogenecity of a Group B Neisseria meningitidis Outer Membrane Vesicle Vaccine", Developments in Biological Standardization, vol. 92, pp. 323-333, (1998).
Sierra GV, et al. (1991). Vaccine against group B Neisseria meningitidis: protection trial and mass vaccination results in Cuba. NIPH Ann 14: 195-207.
Slide printout by Carpmaels & Ransford, filed in opposition against EP1534326, dated Nov. 23, 2009, 2 pages.
Statement of Grounds of Appeal by Carpmaels & Ransford, filed in Opposition against EP1644035, dated May 30, 2014, 5 pages.
Statement of Grounds of Appeal by GlaxoSmithKline Biologicals S.A., filed in relation to EP1534326, dated Aug. 4, 2010, 24 pages.
van de Waterbeemd (2012). "Identification and optimization of critical process parameters for the production of NOMV vaccine against Neisseria meningitidis," Vaccine, 30(24):3683-90.
Van der Ley & Steeghs (2003) "Lessons from an LPS-deficient Neisseria meningitidis mutant" Journal of Endotoxin Research 9(2):124-128.
Van der Ley et al. (1992). "Construction of a Multivalent Meningococcal Vaccine Strain Based on the Class I Outer Membrane Protein," Infection and Immunity 60(8): 3516-3161.
Verheul et al. (1991). "Preparation, Characterization, and Immunogenicity of Meningococcal Immunotype L2 and L3,7,9 Phosphoethanolamine Group-Containing Oligosaccharide-Protein Conjugates," Infection and Immunity 59(3):843-851.
Wedege et al. (2003). "Antibody specificities and effect of meningococcal carriage in Icelandic teenagers receiving the Norwegian serogroup B outer membrane vesicle vaccine," Infect. Immun. 71:3775-3781.
Williams et al., (2007) "Proteomic analysis of outer membranes and vesicles from wild-type serogroup B Neisseria meningitidis and a lipopolysaccharide-deficient mutant" Infection and Immunity 75(3):1364-1372.
Wilson & Walker (Eds.) (1994). "Wilson Principles and techniques of practical biochemistry: Editors: Bryan L. Williams and Keith Wilson," Cambridge University Press, Cambridge, fourth edition, pp. 309.
Written submission in preparation to oral proceedings by Carpmaels & Ransford, filed in Opposition against EP1644035, dated Oct. 18, 2013, 2 pages.
Written submission in preparation to oral proceedings by GlaxoSmithKline Biologicals S.A., filed in opposition against EP1534326, dated Sep. 30, 2009, 24 pages.
Written submission in preparation to oral proceedings by Nederlandsch Octrooibureau, filed in Opposition against EP1644035, dated Oct. 18, 2013, 6 pages.
Zollinger et al. (2010). "Design and evaluation in mice of a broadly protective meningococcal group B native outer membrane vesicle vaccine," Vaccine, 28(31):5057-5067.
"VA-MENGOC-BC," Product information from S.C.S. Farmacia Manes, Argentina. 1 page.

CECMED (Dec. 2, 2011), "Resumen de las Caracteristicas del Producto: VA-MENGOC-BC," Ministerio de Salud Publica de Cuba, 4 pages. (3 page English translation included).
Debbag et al. (1994). "Evaluacion de las reacciones adversas asociadas con la vacuna antimeningococcica BC. Informe perliminar sobre 8,117 vacunados." Rev Hosp Ninos BAires, No. 158/159, 6 pages. (6 page English translation included).
Galeano et al. (1995). "Efectividad de una vacuna antimeningococcica en una cohorte de itagui, Colombia, 1995," Epidemiologico de Antioquia 20(2), 8 pages (9 page English translation included).
Gil et al. (2009). "Proteomic study via a non-gel based approach of meningococcal outer membrane vesicle vaccine obtained from strain CU385," Human Vaccines 5(5):347-356.
International Preliminary Examination Report mailed Aug. 23, 2000, for international patent application No. PCT/US99/11977, filed May 28, 1999, 7 pages.
McLeod et al. (2000). "Structural relationships and sialylation among meningococcal L1, L8 and L3,7 lipooligosaccharide serotypes," J Biol Chem, 275(13):9716-24, McLeod Griffis.
Ochoa, Rolando (2008). "Main projects on research, development and manufacturing of human vaccines," excerpt from presentation at BioQatar Symposium 2008, 4 slides.
Perez et al. (2010). "Community acquired bacterial meningitis in Cuba: a follow up of a decade," BMC Infectious Diseases 10:130, 9 pages.
Rodriguez et al. (1999). "The epidemiological impact of antimeningococal B vaccination in Cuba," Mem Inst Oswaldo Cruz 94(4):433-440.
Vermont et al. (2003). "Meningococcal serogroup B infections: a search for a broadly protective vaccine," Expert Rev Vaccines, 2(5):673-81.
Artenstein, M.S. (1975). "Control of Meningococcal Meningitis with Meningococcal Vaccines." Yale J. Biol. Med. 48(3):197-200.
Bai et al. (2011) "Recombinant protein meningococcal serogroup B vaccine combined with outer membrane vesicles." Expert Opin Biol Ther. 11:969-85.
Castro et al. (2009), "Western Blot technique as an identity criterion for Men B antimeningococcal vaccine," Cuban Journal of Pharmacy, 43(3). Accessed May 5, 2016. 6 pages plus 13 pages of English translation.
Decision revoking EP1534326, filed in Opposition against EP1534326, dated Jan. 15, 2016, 3 pages.
Decision revoking EP1644035, filed in Opposition against EP1644035, dated Jan. 20, 2014, 14 pages.
Ellis et al. (2010). "Virulence and immunomodulatory roles of bacterial outer membrane vesicles," Microbiol Mol Biol Rev, 74(1):81-94.
Ferrari et al. (2006). "Outer membrane vesicles from group B Neisseria meningitidis delta gna33 mutant: proteomic and immunological comparison with detergent-derived outer membrane vesicles," Proteomics, 6(6):1856-66.
Gorringe & Pajon (2012) "Bexsero: a multicomponent vaccine for prevention of meningococcal disease." Human Vaccines & Immunotherapeutics 8:1-10.
Kimura et al. (2011) "Immunogenicity and Safety of a Multicomponent Meningococcal Serogroup B Vaccine and a Quadrivalent Meningococcal CRM197 Conjugate Vaccine against Serogroups A, C, W-135, and Y in Adults Who Are at Increased Risk for Occupational Exposure to Meningococcal Isolates" Clin. Vaccine Immunol. 18(3):483-486.
Muralinath et al. (2011), "Immunization with *Salmonella* enterica serovar Typhimurium-derived outer membrane vesicles delivering the pneumococcal protein PspA confers protection against challenge with *Streptococcus* pneumoniae." Infect Immun. 79(2):887-94.
Pinto et al. (2011) "An experimental outer membrane vesicle vaccine from N. meningitidis serogroup B strains that induces serum bactericidal activity to multiple serogroups." Vaccine 29:7752-8.
Poolman et al. (1986). "Class 1/3 outer membrane protein vaccine against group B, type 15, subtype 16 meningococci." Dev. Biol. Stand. Abstract only. 63:147-52.
Tavano et al. (Jul. 2000). "The membrane expression of Neisseria meningitidis adhesin A (NadA) increases the proimmune effects of

(56) References Cited

OTHER PUBLICATIONS

MenB OMVs on human macrophages, compared with NadA-OMVs, without further stimulating their proinflammatory activity on circulating monocytes," J Leukoc Biol 86(1):143-153.

Claassen et al. (1996). "Production, characterization and control of a Neisseria meningitidis hexavalent class 1 outer membrane protein containing vesicle vaccine," Vaccine 14(10): 1001-1008.

Andersen et al (2000). "Immune responses to meningococcal outer membrane vesicles after intranasal immunization," Twelfth International Pathogenic Neisseria Conference, vol. #57, page 31.

* cited by examiner

ULTRAFILTRATION FOR PREPARING OUTER MEMBRANE VESICLES

This application is a national stage application of co-pending PCT application PCT/IS2004/002475 filed Jul. 15, 2004, which was published in English under PCT Article 21(2) on Jan. 20, 2005, which claims priority to GB ser. no. 0316560.2, filed Jul. 15, 2003. The disclosures of these applications are expressly incorporated herein.

All documents cited herein are incorporated by reference in their entirety.

TECHNICAL FIELD

This invention is in the field of vesicle preparation for immunisation purposes.

BACKGROUND ART

One of the various approaches to immunising against *N. meningitidis* infection is to use outer membrane vesicles (OMVs). An efficacious OMV vaccine against serogroup B has been produced by the Norwegian National Institute of Public Health [e.g. ref. 1] but, although this vaccine is safe and prevents NmB disease, its efficacy is limited to the strain used to make the vaccine.

The 'RIVM' vaccine is based on vesicles containing six different PorA subtypes and has been shown to be immunogenic in children in phase II clinical trials [2].

References 3 & 4 disclose a vaccine against different pathogenic serotypes of serogroup meningococcus based on OMVs which retain a protein complex of 65-kDa. Reference 5 discloses a vaccine comprising OMVs from genetically-engineered meningococcal strains, with the OMVs comprising: at least one Class I outer-membrane protein (OMP) but not comprising a Class 2/3 OMP. Reference 6 discloses OMVs comprising OMPs which have mutations in their surface loops. Reference 7 discloses compositions comprising OMVs supplemented with transferrin binding proteins (e.g. TbpA and TbpB) and/or Cu,Zn-superoxide dismutase. Reference 8 discloses compositions comprising OMVs supplemented by various proteins. References 9 & 10 also describe OMV preparations from meningococcus.

Reference 11 discloses a process for preparing OMV-based vaccines, particularly for serogroup A meningococcus, comprising the following 10 steps: (a) cultivating bacterial cells; (b) concentrating the cultivated cells from step (a); (c) treating the cells with a bile acid salt detergent at a pH sufficiently high not to precipitate the detergent, for inactivating the bacteria, disrupting the outer membrane of the bacteria and forming vesicles of the outer membrane of the bacteria, said vesicles comprising outer membrane components mainly presented in their native form; (d) centrifuging the composition from step (c) at 10,000-20,000×g for about 1 to 2 hours to separate the outer membrane vesicles from the treated cells and cell debris, and collecting the supernatant; (e) performing a high speed centrifugation of the supernatant from step (d) and collecting the outer membrane vesicles in a pellet; (f) re-dispersing the pellet from step (e) in a buffer by stirring at ambient temperature; (g) performing a second high speed centrifugation in accordance with step (e), collecting the outer membrane vesicles in a pellet; (h) re-dispersing the pellet from step (g) in an aqueous medium containing a stabilising agent by stirring at ambient temperature; (i) performing a step-wise sterile filtration through at least two filters of decreasing pore size of the re-dispersed composition from step (h), ending with a filter of pore-size of about 0.2 μm; and (j) optionally including the composition from step (i) in a pharmaceutically acceptable carrier and/or adjuvant composition.

It is an object of the present invention to provide an improved process for preparing OMVs for use in vaccines, in particular a process which can prepare a greater quantity of OMVs in a shorter time, and particularly a process suitable for industrial-scale use.

DISCLOSURE OF THE INVENTION

The invention is based on the finding that, compared to the centrifugation used in step (e) of the process of reference 11, ultrafiltration allows much larger amounts of OMV-containing supernatant to be processed in a much shorter time (typically >15 liters in 4 hours, compared to <1.5 liters in 10 hours). As well allowing step (e) to be performed more quickly, the use of ultrafiltration allows step (f) to be avoided because the OMVs remains in suspension.

Thus the invention provides a process for preparing bacterial OMVs, comprising a step of ultrafiltration. The ultrafiltration step is performed on an aqueous suspension of OMVs after they have been prepared from bacteria and the OMVs remain in suspension after the ultrafiltration step.

The invention also provides, in a process for preparing OMVs from a bacterium, the improvement consisting of the use of ultrafiltration of an OMV suspension in place of a step of centrifugation.

The invention also provides a process for purifying bacterial OMVs, wherein the process does not include a centrifugation step in which the OMVs are pelleted, particularly a centrifugation step performed on crude OMVs.

The Ultrafiltration Step

Ultrafiltration is a separation process whereby solvent is removed from a solution (including a colloidal solution) or a suspension by forcing it to flow through a membrane by the application of a hydraulic pressure. Components in the solution which are significantly larger than the solvent cannot pass through the membrane. Ultrafiltration therefore separates components based on size.

The ultrafiltration step preferably results in diafiltration of the solution. In diafiltration, solvent and/or microsolutes (e.g. salts) which are removed during ultrafiltration are replaced by new solvent and microsolutes. In general, removal and replacement occur at the same rate and the volume of the solution is thus kept constant. The overall effect of the process is therefore the replacement of original solvent/microsolutes with new solvent/microsolutes. The process of the invention may thus include a step of diafiltration.

The ultrafiltration is preferably cross-flow or tangential flow ultrafiltration, in which the solution flows substantially parallel to the membrane surface, rather than flowing perpendicular to the surface as in ordinary filtration.

Preferred membranes for use in the ultrafiltration step have a cut-off of about 300 kDa.

The ultrafiltration step preferably last less than 10 hours e.g. between 2 and 6 hours, preferably between 3 and 5 hours e.g. between 3.5 and 4.5 hours.

Membranes may be made from any suitable material e.g. polyethersulphone.

Pre-Ultrafiltration Steps

Prior to the ultrafiltration step, the process of the invention will typically comprise an initial step of cultivating bacterial cells (e.g. in broth or in solid medium culture), optionally followed by a step of collecting and/or concentrating the cultivated cells (e.g. by filtration or by a low-speed centrifugation to pellet the cells). However, the invention may be performed on bacteria which have already been cultured and/or harvested separately. The bacterial culture preferably involves the use of neither blood products nor material contaminated with a transmissible spongiform encephalopathy agent.

The ultrafiltration step is performed on an aqueous suspension of OMVs after they have been prepared from bacteria. Prior to ultrafiltration, the process may therefore comprise a step of OMV preparation in which cells are treated to disrupt their outer membranes. The preparation of OMVs from meningococcus is well-known in the art. Methods for obtaining suitable preparations are disclosed in, for instance, references 1 to 25. Techniques for forming OMVs include treating bacteria with a bile acid salt detergent (e.g. salts of lithocholic acid, chenodeoxycholic acid, ursodeoxycholic acid, deoxycholic acid, cholic acid, ursocholic acid, etc., with sodium deoxycholate [26 & 27] being preferred for treating *Neisseria*) at a pH sufficiently high not to precipitate the detergent [11]. Other techniques may be performed substantially in the absence of detergent [28] using techniques such as sonication, homogenisation, microfluidisation, cavitation, osmotic shock, grinding, French press, blending, etc.

After OMV formation and prior to ultrafiltration, the OMVs are preferably separated from bacterial cells and cell debris. Separation can conveniently be achieved by centrifugation (e.g. at 10,000-20,000×g for about 1 to 2 hours). OMVs remain in the supernatant and can then be subjected to ultrafiltration according to the invention, rather than to ultracentrifugation as in the prior art. Other methods for separating outer membrane fractions from cytoplasmic molecules may involve filtration (e.g. cross flow filtration), differential precipitation or aggregation of outer membranes and/or OMVs, affinity separation methods using ligands that specifically recognize outer membrane molecules, etc. Use of a closed filtration system may be preferred to avoid open handling of infectious bacteria.

In order to preserve the native conformation of proteins and other labile outer membrane antigens, mild conditions will generally be selected for preparation of OMVs. Heat inactivation of bacteria (e.g. at 56° C. or higher) is thus preferentially avoided, as is solvent denaturation.

Post-Ultrafiltration Steps

After the ultrafiltration step, the OMVs may be further treated.

For example, the OMVs may be sterilised. Sterilisation is preferably a final step before packaging as a pharmaceutical, and can conveniently be achieved by filter sterilisation. Although OMVs will pass through a standard 0.22 µm filters, these can rapidly become clogged by other material, and so it is preferred to perform sequential steps of filter sterilisation through a series of filters of decreasing pore size, finishing with a standard sterilisation filter (e.g. a 0.22 µm filter). Examples of preceding filters would be those with pore size of 0.8 µm, 0.45 µm, etc. Filter sterilisation advantageously occurs at ambient temperature or above, rather than at refrigeration temperatures. Vesicle flexibility is higher at ambient temperature and larger vesicles (~0.2 µm) can thus pass through a 0.22 µm filter more easily, giving less clogging of filters.

The OMVs may also be centrifuged (e.g. ultracentrifuged) after ultrafiltration takes place. Thus, in some embodiments, the invention does not completely replace the use of ultracentrifugation during OMV preparation, but removes at least one step of ultracentrifugation relative to ref. 11. A normal ultracentrifugation step requires about 13 hours for 1.3 liters of OMV suspension, and so a large volume of OMVs requires a large ultracentrifugation resource. Ultrafiltration according to the invention can be used to reduce the volume which has to be ultracentrifuged (by around 3-fold) and so can improve throughput even though ultracentrifugation is not wholly avoided.

The OMVs may be combined with pharmaceutical carriers and/or adjuvants and/or stabilisers. For example, pellet(s) from ultracentrifugation can be re-suspended (e.g. in a sucrose solution, preferably about 3% sucrose) and then subjected to filter sterilisation as described above.

OMVs may be sonicated. Sonication is particularly useful between re-suspension of centrifugation pellets and sterilisation.

After re-suspension, OMV preparations preferably contain between 500 and 2000 mg of protein per milliliter e.g. between 900 and 1800 mg/ml, or 1000±100 mg/ml.

Overall Process for Preparing Sterile OMVs

In general, therefore, the process of the invention will include the following steps: (1) cultivating bacterial cells; (2) collecting the cultivated cells; (3) OMV formation; (4) separation of OMV from cell debris, to give an aqueous suspension of OMV; (5) ultrafiltration; (6) centrifugation and re-suspension to collect purified OMV; and (7) sterilisation. pH may be adjusted at any stage as required. Similarly, dilution as appropriate can be used.

Step (5) in this process replaces steps (e) and (f) from reference 11.

The Bacterium

The bacterium from which OMVs are prepared may be Gram-positive, but it is preferably Gram-negative. The bacterium may be from any suitable genus, including *Moraxella* (e.g. *M. catarrhalis* [29,30]), *Shigella* (e.g. *S. flexneri* [31,32]), *Pseudomonas* (e.g. *P. aeruginosa* [31,32]), *Treponema* (e.g. *T. pallidum* [33]), *Haemophilus* (e.g. *H. influenzae* [9 & 10]), *Porphyromonas* (e.g. *P. gingivalis* [34]) or *Helicobacter* (e.g. *H. pylori* [35]), but it is preferably from the *Neisseria* genus. Preferred *Neisseria* species are *N. meningitidis, N. lactamica* [36] and *N. gonorrhoeae* [37 & 38]. Within *N. meningitidis*, any of serogroups A, C, W135 and Y may be used, but it is preferred to prepare vesicles from serogroup B.

Preferred strains within serogroup B are MC58, 2996, H4476, 394/98 and New Zealand strain 98/254. The best serotypes and strains to use, however, will depend on the strains prevalent in a particular geographical location. For example, the meningococcus can be of any serotype (e.g. 1, 2a, 2b, 4, 14, 15, 16, etc.), of any serosubtype (P1.2; P1.4; P1.5; P1.5,2; P1.7,16; P1.7,16b; P1.9; P1.9,15; P1.12,13; P1.13; P1.14; P1.15; P1.21,16; P1.22,14; etc.) and of any immunotype (e.g. L1; L3,3,7; L10; etc.), and preferred strains include: (a) B:4:P1.4; (b) B:4:P1.15; (c) B:15:P1.7, 16; and (d) B:4:P1.7b,4. The meningococcus may be from any suitable lineage, including hyperinvasive and hypervirulent lineages e.g. any of the following seven hypervirulent lineages: subgroup I; subgroup III; subgroup IV-1; ET-5 complex; ET-37 complex; A4 cluster; lineage 3. These lineages have been defined by multilocus enzyme electrophoresis (MLEE), but multilocus sequence typing (MLST) has also been used to classify meningococci [ref. 39] e.g. the ET-37 complex is the ST-11 complex by MLST, the ET-5 complex is ST-32 (ET-5), lineage 3 is ST-41/44, etc.

To reduce pyrogenic activity, it is preferred that the bacterium should have low endotoxin (LPS) levels. Suitable mutant bacteria are known e.g. mutant *Neisseria* [40] and mutant *Helicobacter* [41]. Processes for preparing LPS-depleted outer membranes from Gram-negative bacteria are disclosed in reference 42.

The bacterium may be a wild-type bacterium, or it may be a recombinant bacterium. Preferred recombinant bacteria over-express (relative to the corresponding wild-type strain) immunogens such as NspA, protein 287 [8], protein 741 [8], TbpA, TbpB, superoxide dismutase [7], etc. The bacterium may express more than one PorA class I outer membrane protein e.g. 2, 3, 4, 5 or 6 of PorA subtypes: P1.7,16; P1.5,2; P1.19,15; P1.5c,10; P1.12,13; and P1.7h,4 [e.g. refs. 12 & 14].

Other recombinant bacteria that can be used with the invention have one or more mutations to decrease (or, preferably, to knockout) expression of particular gene products. Preferred genes for down-regulation and/or knockout include: (a) Cps, CtrA, CtrB, CtrC, CtrD, FrpB, GalE, HtrB/MsbB, LbpA, LbpB, LpxK, Opa, Opc, PilC, PorA, PorB, SiaA, SiaB, SiaC, SiaD, TbpA, and/or TbpB [9]; (b) CtrA, CtrB, CtrC, CtrD, FrpB, GalE, HtrB/MsbB, LbpA, LbpB, LpxK, Opa, Opc, PhoP, PilC, PmrE, PmrF, PorA, SiaA, SiaB, SiaC, SiaD, TbpA, and/or TbpB [10]; (c) lytic transglycosylase NMB0033 [43]; (d) ExbB, ExbD, rmpM, CtrA, CtrB, CtrD, GalE, LbpA, LpbB, Opa, Opc, PilC, PorA, PorB, SiaA, SiaB, SiaC, SiaD, ThpA, and/or TbpB [44]; and (e) CtrA, CtrB, CtrD, FrpB, OpA, OpC, PilC, PorA, PorB, SiaD, SynA, SynB, and/or SynC [45].

Pharmaceutical Compositions

For human use, OMVs will generally be combined with a pharmaceutically acceptable carrier.

The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which can be administered without undue toxicity. Suitable carriers can be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers in therapeutic compositions can include liquids such as water, saline, glycerol and ethanol. Auxiliary substances, such as wetting or emulsifying agents, pH buffering substances, and the like, can also be present in such vehicles. Typically, the therapeutic compositions are prepared as injectables, either as liquid solutions or suspensions; solid forms suitable for solution in, or suspension in, liquid vehicles prior to injection can also be prepared. Liposomes are included within the definition of a pharmaceutically acceptable carrier. Pharmaceutically acceptable salts can also be present in the pharmaceutical composition, e.g. mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in reference 46. The composition will typically include saline.

Once formulated, compositions can be administered directly to a subject. Delivery will generally be accomplished by parenteral injection (e.g. subcutaneously, intraperitoneally, intravenously or intramuscularly, or to the interstitial space of a tissue) or by mucosal administration (e.g. oral, pulmonary, rectal, vaginal, intranasal [47,48]), etc.). Transdermal applications, needles, and gene guns or hyposprays may also be used. Intramuscular injection is the preferred manner of delivery.

The dose and the means of administration of the inventive pharmaceutical compositions are determined based on the specific qualities of the therapeutic composition, the condition, age, and weight of the patient, the progression of the disease, and other relevant factors.

Neisserial infections affect various areas of the body and so the compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition). The composition may be prepared for topical administration e.g. as an ointment, cream or powder. The composition be prepared for oral administration e.g. as a tablet or capsule, or as a syrup (optionally flavoured). The composition may be prepared for pulmonary administration e.g. as an inhaler, using a fine powder or a spray. The composition may be prepared as a suppository or pessary. The composition may be prepared for nasal, aural or ocular administration e.g. as drops.

The OMVs of the invention may be combined with an adjuvant. Preferred adjuvants to enhance effectiveness of the composition include, but are not limited to: (A) MF59 (5% Squalene, 0.5% Tween 80, and 0.5% Span 85, formulated into submicron particles using a microfluidizer) [see Chapter 10 of ref. 49; see also ref. 50]; (B) microparticles (i.e. a particle of ~100 nm to ~150 μm in diameter, more preferably ~200 nm to ~30 μm in diameter, and most preferably ~500 nm to ~10 μm in diameter) formed from materials that are biodegradable and non-toxic (e.g. a poly(α-hydroxy acid), a polyhydroxybutyric acid, a polyorthoester, a polyanhydride, a polycaprolactone, etc.), with poly(lactide-co-glycolide) being preferred, optionally treated to have a negatively-charged surface (e.g. with SDS) or a positively-charged surface (e.g. with a cationic detergent, such as CTAB) [51 & 52]); (C) liposomes [see Chapters 13 and 14 of ref. 49]; (D) ISCOMs [see Chapter 23 of ref. 49], which may be devoid of additional detergent [53]; (E) SAF, containing 10% Squalane, 0.4% Tween 80, 5% pluronic-block polymer L121, and thr-MDP, either microfluidized into a submicron emulsion or vortexed to generate a larger particle size emulsion [see Chapter 12 of ref. 49]; (F) Ribi™ adjuvant system (RAS), (Ribi Immunochem) containing 2% Squalene, 0.2% Tween 80, and one or more bacterial cell wall components from the group consisting of monophosphorylipid A (MPL), trehalose dimycolate (CIDM), and cell wall skeleton (CWS), preferably MPL+CWS (Detox™); (G) saponin adjuvants, such as QuilA or QS21 [see Chapter 22 of ref. 49], also known as Stimulon™; (H) chitosan [e.g. 54]; (I) complete Freund's adjuvant (CFA) and incomplete Freund's adjuvant (IFA); (J) cytokines, such as interleukins (e.g. IL-1, IL-2, IL-4, IL-5, IL-6, IL-7, IL-12, etc.), interferons (e.g. interferon-γ), macrophage colony stimulating factor, tumor necrosis factor, etc. [see Chapters 27 & 28 of ref. 49]; (K) a saponin (e.g. QS21)+3dMPL+IL-12 (optionally+a sterol) [55]; (L) monophosphoryl lipid A (MPL) or 3-O-deacylated MPL (3dMPL) [e.g. chapter 21 of ref. 49]; (M) combinations of 3dMPL with, for example, QS21 and/or oil-in-water emulsions [56]; (N) oligonucleotides comprising CpG motifs [57] i.e. containing at least one CG dinucleotide; (O) a polyoxyethylene ether or a polyoxyethylene ester [58]; (P) a polyoxyethylene sorbitan ester surfactant in combination with an octoxynol [59] or a polyoxyethylene alkyl ether or ester surfactant in combination with at least one additional non-ionic surfactant such as an octoxynol [60]; (Q) an immunostimulatory oligonucleotide (e.g. a CpG oligonucleotide) and a saponin [61]; (R) an immunostimulant and a particle of metal salt [62]; (S) a saponin and an oil-in-water emulsion [63]; (T) *E. coli* heat-labile enterotoxin ("LT"), or detoxified mutants thereof, such as the K63 or R72 mutants [e.g. Chapter 5 of ref. 64]; (U) cholera toxin ("CT"), or detoxified mutants thereof [e.g. Chapter 5 of ref. 64]; (V) double-stranded RNA; (W) aluminium salts, such as aluminium hydroxides (including oxyhydroxides), aluminium phosphates (including hydroxyphosphates), aluminium sulfate, etc [Chapters 8 & 9 in ref. 49]; (X) monophosphoryl lipid A mimics, such as aminoalkyl glucosaminide phosphate derivatives e.g. RC-529 [65]; (y) polyphosphazene (PCPP); (Z) a bioadhesive [66] such as esterified hyaluronic acid microspheres [67] or a mucoadhesive selected from the group consisting of crosslinked derivatives of poly(acrylic acid), polyvinyl alcohol, polyvinyl pyrollidone, polysaccharides and carboxymethylcellulose. Other substances that act as immunostimulating agents may also be used [e.g. see Chapter 7 of ref. 49].

Aluminium salts are preferred adjuvants for parenteral immunisation. Mutant toxins are preferred mucosal adjuvants. The use of an aluminium hydroxide adjuvant is most preferred, particularly for intramuscular injection, and this adjuvant is preferably used with a histidine buffer [68].

The invention provides a process for preparing a pharmaceutical composition, comprising the steps of: (i) preparing OMVs according to the invention; and (ii) formulating the OMVs as a pharmaceutical. Step (ii) may involve activities such as filtration, addition of adjuvants, addition of buffer, etc.

OMVs and OMV-Based Compositions

The invention provides OMVs obtained by a process of the invention. The invention also provides OMVs obtainable by a process of the invention, which generally comprise outer membrane components in essentially their native form.

The invention also provides a composition comprising such OMVs and a pharmaceutically acceptable carrier. The composition may also comprise an adjuvant.

Compositions of the invention are preferably immunogenic compositions, and are more preferably vaccine compositions. Such compositions can be used to raise immune responses (e.g. antibody responses) in a mammal (e.g. in a human, such as a child).

The pH of the composition is preferably between 6 and 8, preferably about 7. The pH may be maintained by the use of a buffer. The composition may be sterile and/or pyrogen-free. The composition may be isotonic with respect to humans. The composition may or may not include a preservative (e.g. thiomersal, 2-phenoxyethanol, etc.). Mercury-free compositions are preferred.

The composition is preferably free from blood-derived components. The composition is preferably free from transmissible spongiform encephalopathy agents (e.g. prions). The composition is preferably substantially free from whole bacteria, and in particular from living bacteria.

The composition may include residual material from vesicle preparation (e.g. detergent, preferably <0.4 µg detergent per µg OMV protein). The composition may include soluble sugars e.g. disaccharides such as sucrose and/or trehalose. LPS content is preferably <0.2 kg per µg OMV protein.

Compositions of the invention may be distributed in various containers e.g. vials or pre-filled syringes. The use of glass vials is preferred. These containers will generally be sterile and hermetically-sealed. Each container preferably includes a single dose e.g. 0.5 ml of liquid. Containers may be packaged singly or in multiples e.g. a box of 10 vials. Once packaged, compositions of the invention are preferably stored at between 2° C. and 8° C., but should not be frozen.

Vaccines of the invention may be prophylactic (i.e. to prevent disease) or therapeutic (i.e. to reduce or eliminate the symptoms of a disease).

Compositions for administration to patients will comprise an immunologically effective amount of the OMVs. An "immunologically effective amount" is an amount sufficient to effect an immune response in a patient, and more preferably a protective immune response in a patient. The precise amount for a patient will depend upon their size and health, the nature and extent of their condition, and the therapeutics or combination of therapeutics selected for administration. The effective amount for a given situation is determined by routine experimentation and is within the judgment of a physician. For purposes of the present invention, an immunologically effective amount will generally be administered at a dosage of from about 0.01 mg/kg to about 5 mg/kg, or about 0.01 mg/kg to about 50 mg/kg or about 0.05 mg/kg to about 10 mg/kg of the composition of the invention in the individual to which it is administered. A typical composition will include 50 µg/ml of protein.

In addition to OMV antigens, compositions of the invention may include one or more of the following additional antigens:

a saccharide antigen from *N. meningitidis* serogroup A, C, W135 and/or Y, such as the oligosaccharide disclosed in ref 142 from serogroup C [see also ref. 69] or the oligosaccharides of ref 146.

antigens from *Helicobacter pylori* such as CagA [70 to 73], VacA [74, 75], NAP [76, 77, 78], HopX [e.g. 79], HopY [e.g. 79] and/or urease.

a saccharide antigen from *Streptococcus pneumoniae* [e.g. 80, 81, 82].

an antigen from hepatitis A virus, such as inactivated virus [e.g. 83, 84].

an antigen from hepatitis B virus, such as the surface and/or core antigens [e.g. 84, 85].

an antigen from hepatitis C virus [e.g. 86].

a diphtheria antigen, such as a diphtheria toxoid [e.g. chapter 3 of ref. 87].

a tetanus antigen, such as a tetanus toxoid [e.g. chapter 4 of ref. 87].

an antigen from *Bordetella pertussis*, such as pertussis holotoxin (PT) and filamentous haemagglutinin (FHA) from *B. pertussis*, optionally also in combination with pertactin and/or agglutinogens 2 and 3 [e.g. refs. 88 & 89]; whole-cell pertussis antigen may also be used.

a saccharide antigen from *Haemophilus influenzae* B [e.g. 69].

polio antigen(s) [e.g. 90, 91] such as OPV or, preferably, IPV.

an antigen from *N. gonorrhoeae* [e.g. 92, 93, 94, 95].

an antigen from *Chlamydia pneumoniae* [e.g. refs. 96 to 102].

an antigen from *Porphyromonas gingivalis* [e.g. 103].

rabies antigen(s) [e.g. 104] such as lyophilised inactivated virus [e.g. 105, RabAvert™].

measles, mumps and/or rubella antigens [e.g. chapters 9, 10 & 11 of ref. 87].

influenza antigen(s) [e.g. chapter 19 of ref. 87], such as the haemagglutinin and/or neuraminidase surface proteins.

antigen(s) from a paramyxovirus such as respiratory syncytial virus (RSV [106, 107]) and/or parainfluenza virus (PIV3 [108]).

an antigen from *Moraxella catarrhalis* [e.g. 109].

an antigen from *Streptococcus pyogenes* (group A streptococcus) [e.g. 110, 111, 112].

an antigen from *Staphylococcus aureus* [e.g. 113].

an antigen from *Bacillus anthracis* [e.g. 114, 115, 116].

an antigen from a virus in the flaviviridae family (genus flavivirus), such as from yellow fever virus, Japanese encephalitis virus, four serotypes of Dengue viruses, tick-borne encephalitis virus, West Nile virus.

a pestivirus antigen, such as from classical porcine fever virus, bovine viral diarrhoea virus, and/or border disease virus.

a parvovirus antigen e.g. from parvovirus B19.

a prion protein (e.g. the CJD prion protein)

an amyloid protein, such as a beta peptide [117]

a cancer antigen, such as those listed in Table I of ref. 118 or in tables 3 & 4 of ref. 119.

The inclusion of further *N. meningitidis* antigens is preferred. In particular, the composition may include a saccharide antigen from one or more (i.e. 1, 2, 3 or 4) of meningococcal serogroups A, C, W135 and/or Y. Where fewer than 4 of these additional serogroups are included, it is preferred to include at least serogroup C e.g. C+A+W135, C+A+Y, C+W135+Y.

Where a saccharide or carbohydrate antigen is used, it is preferably conjugated to a carrier protein in order to enhance immunogenicity [e.g. refs. 120 to 129]. Preferred carrier proteins are bacterial toxins or toxoids, such as diphtheria or tetanus toxoids. The $CRM_{197}$ diphtheria toxin mutant is particularly preferred [130]. Other carrier polypeptides include the *N. meningitidis* outer membrane protein [131], synthetic peptides [132, 133], heat shock proteins [134, 135], pertussis proteins [136, 137], protein D from *H. influenzae* (138), cytokines [139], lymphokines [139], hormones [139], growth factors [139], toxin A or B from *C. difficile* [140], iron-uptake proteins [141], etc. Different saccharides can be conjugated to the same or different type of carrier protein. Any suitable conjugation reaction can be used, with any suitable linker where necessary. For meningococcal conjugates [142-148], preferred carriers are diphtheria toxoid, CRM197 and *H. influenzae* protein D.

Toxic protein antigens may be detoxified where necessary e.g. detoxification of pertussis toxin by chemical and/or genetic means [89].

Where a diphtheria antigen is included in the composition it is preferred also to include tetanus antigen and pertussis antigens. Similarly, where a tetanus antigen is included it is preferred also to include diphtheria and pertussis antigens. Similarly, where a pertussis antigen is included it is preferred also to include diphtheria and tetanus antigens. DTP combinations are thus preferred.

Antigens in the composition will typically be present at a concentration of at least 1 g/ml each. In general, the concentration of any given antigen will be sufficient to elicit an immune response against that antigen.

As an alternative to using protein antigens in the composition of the invention, nucleic acid encoding the antigen may be used [e.g. refs. 149 to 157]. Protein components of the compositions of the invention may thus be replaced by nucleic acid (preferably DNA e.g. in the form of a plasmid) that encodes the protein.

Methods of Treatment

The invention provides a method for raising an immune response in a patient, comprising administering an immunogenic dose of OMVs of the invention to the patient. The immune response is preferably protective and preferably involves antibodies and/or cell-mediated immunity. The method may raise a booster response.

The patient is preferably a human. Where the vaccine is for prophylactic use, the human is preferably a child (e.g. a toddler or infant) or a teenager; where the vaccine is for therapeutic use, the human is preferably a teenager or an adult. A vaccine intended for children may also be administered to adults e.g. to assess safety, dosage, immunogenicity, etc. The patient is preferably less than 20 years old e.g. 13-19 years old, 8-12 years old, 16-24 months old, 6-8 months old, 6 weeks-5 months old.

Vaccines of the invention are preferably administered by intramuscular injection. Typical sites for injection include the upper thigh and the upper arm.

The invention also provides OMVs of the invention for use in medicine.

The invention also provides the use of OMVs of the invention in the manufacture of a medicament for treating and/or preventing meningococcal infection and/or bacterial meningitis.

The invention may be used to elicit systemic and/or mucosal immunity.

Dosage treatment can be a single dose schedule or a multiple dose schedule. Multiple doses may be used in a primary immunisation schedule and/or in a booster immunisation schedule e.g. a primary immunisation schedule may involve three injections, with an interval of about 6 weeks between each injection. A typical volume for a single intramuscular liquid dose is 0.5 ml.

DEFINITIONS

The term "OMV" as used herein includes any proteoliposomic vesicle obtained by disrupting a bacterial outer membrane to form vesicles of the outer membrane which include protein components of the outer membrane. OMVs are prepared artificially from bacteria (e.g. by detergent treatment) and are thus distinct from microvesicles (MVs [158]) and 'native OMVs' ('NOMVs' [48]), both of which are naturally-occurring membrane vesicles that form spontaneously during bacterial growth and are released into culture medium. MVs can be obtained by culturing *Neisseria* in broth culture medium, separating whole cells from the smaller blebs in the broth culture medium, and then collecting the MVs from the cell-depleted medium. Strains for use in production of MVs can generally be selected on the basis of the amount of MVs produced in culture e.g. refs. 159 & 160 describe *Neisseria* with high MV production.

The term "comprising" can mean "including" as well as "consisting" e.g. a composition "comprising" X may consist exclusively of X or may include something additional e.g. X+Y.

The term "about" in relation to a numerical value x means, for example, x±10%.

The word "substantially" does not exclude "completely" e.g. a composition which is "substantially free" from Y may be completely free from Y. Where necessary, the word "substantially" may be omitted from the definition of the invention.

MODES FOR CARRYING OUT TH INVENTION

Example 1

Figure 1:
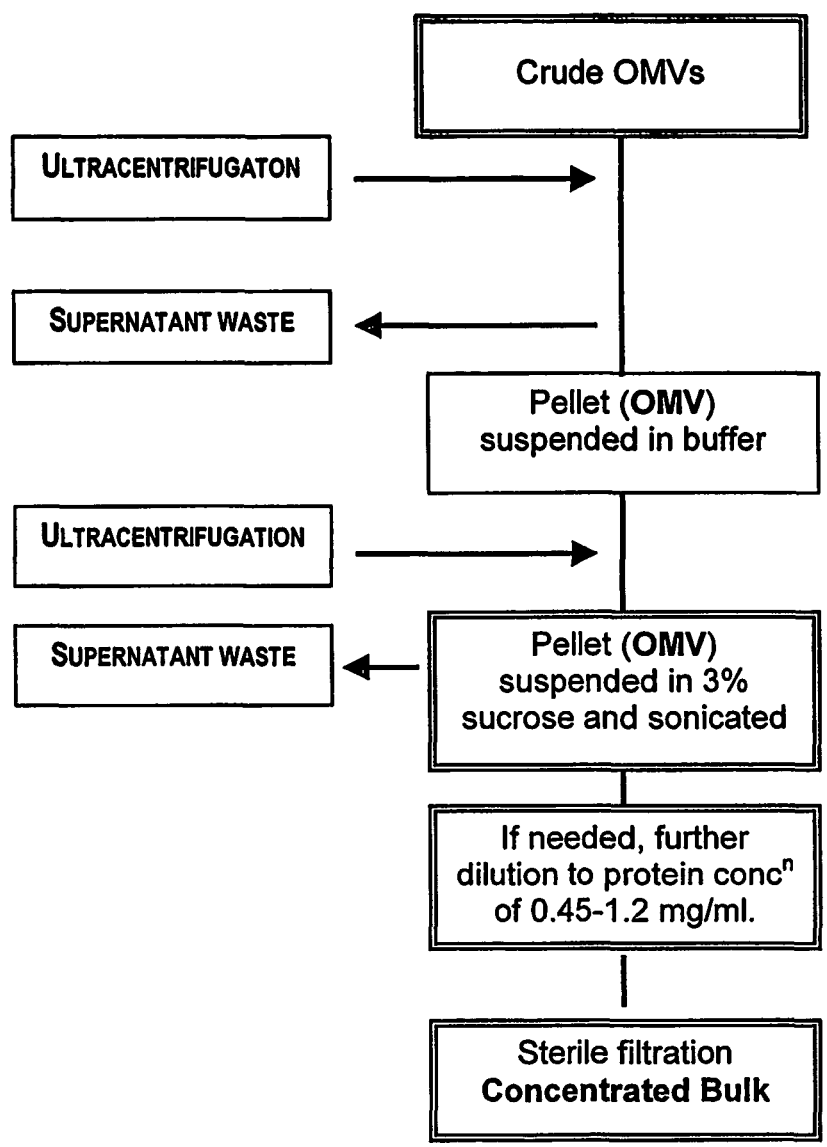
FIG. 1 shows a process including two ultracentrifugation steps without ultrafiltration.

OMVs from Meningococcal Serogroup B
(Norwegian Strain)

*N. meningitidis* serogroup B (strain 44/76, from Norway) was cultured on eight "selective medium for Meningococci" plates at 35° C. in 5% $CO_2$/air atmosphere for 24 hours. Cell were harvested into 2 tubes with 12 ml Frantz' medium. Contents of tubes were added to 2×500 ml flasks containing Frantz' medium (150 ml) and grown with shaking for 12 hours to obtain the correct growth for transferring into 2×5000 ml flasks containing Frantz' medium (1500 ml). The flasks were grown with shaking for a further 12 hours to yield the inoculum. One flask was added to a Chemap fermentor with 300 L capacity, containing 110 L of pre-sterilised Frantz' medium and sterile-filtered dialysed yeast extract. The pH after inoculation was 7.1, maintained at 7.0 with 3N NaOH. A surface aeration fermentation was performed, controlling the amount of air $O_2$ and stirrer applied, and cultivating for 10 hours at 35° C. Growth was terminated at an $OD_{590nm}$ of 7.10, the fermentor was cooled under 15° C., the air supply was reduced and stirring continued at 100 rpm overnight.

Transfer of the bacterial suspension from the fermentor was done by pressure to a Millipore CUF cross flow filtration unit equipped with valves, pumps and a filter module with 4 Pellicon P2B300V05 polyethersulphone filters (300 kD cutoff). Initial transfer of 30 L bacterial suspension was followed with a constant volume concentration until the fermentor was emptied, and then a further concentration was performed to give a volume of 5.5 L.

Concentrating the suspension was performed in the CFF unit by circulating the suspension to be passing by the filters, with a transmembrane pressure being continuously monitored and kept less then 0.5 bar (observed: 0.5 bar at the end of concentration).

Adjustment of pH of the concentrated bacterial suspension from pH 7.0 to 8.2 was done by adding, via a tubing system, 5 L of 0.1 M Tris-HCl buffer of pH 9 with 10 mM EDTA, followed by 15 min stirring in the CFF unit to secure uniform conditions.

Inactivation/extraction of outer membrane (OM) material was initiated by adding, via tubing, 500 ml of an 0.1M Tris-HCl buffer (pH 9) containing 10% deoxycholate (DOC), to give a final concentration of 0.5%. Subsequently the suspension was circulated in the CFF unit for 30 min, and the extracted suspension (9.5 L), checked to be completely without living bacteria, was drained off by pumping into a 25 L bottle.

In a first experiment (experiment A; FIG. 1), crude OMVs were prepared by distributing the inactivated suspension to centrifuge tubes of 500 ml, and centrifuging in a Beckman centrifuge at 9000 rpm (16650×g) for 1 hour at 4° C., collecting 8.5 L of supernatant. 1.35 L of crude OMVs was purified by two subsequent ultracentrifugations at 19000 rpm, 4° C., for 13.6 hours and 6.8 hours respectively, collecting the pellet. The pellet was suspended in 660 ml of 3% sucrose with magnetic stirring at room temperature until homogeneous, obtaining a concentration of the purified material of 1.52 g/L of total protein.

Figure 2:
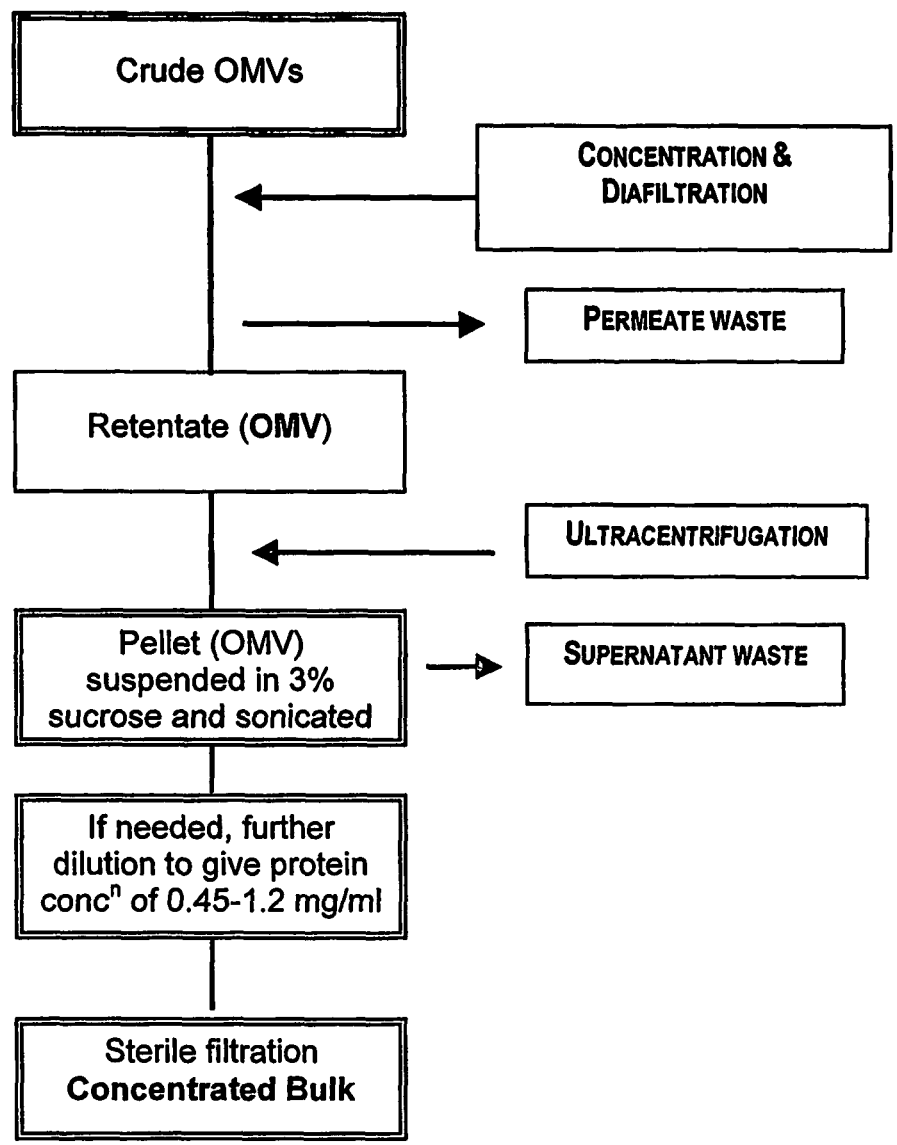
FIG. 2 shows a process in which one ultracentrifugation step has been replaced by an ultrafiltration step.

In a second experiment (experiment B; FIG. 2), 3 L of crude OMVs were prepared from bacterial suspension using a CUF cross flow filtration unit equipped with valves, pumps and a filter module with 1 Pellicon P2B300V05 polyethersulphone filters (300 kD cutoff). Initial transfer of IL crude OMVs was followed with a constant volume concentration until the 3 L was finished, and then diafiltered by adding 5 L of 0.05 M Tris-HCl buffer of pH 8.6 with 2 mM EDTA, 1% of DOC and 20% sucrose. The retentate obtained was purified by ultracentrifugation at 19000 rpm, 4° C., for 6,8 hours, collecting the pellet. The pellet was suspended in 1 L of 3% sucrose with magnetic stirring at room temperature until homogeneous, obtaining a concentration of 0.85 g/L total protein in the purified material.

Final purifications of OMV obtained by both experiment A and B, after a dilution with 3% sucrose around 1.2 g/L of total protein, were both performed at 20° C. by filtering through 3 capsule filters (Gelman Science Suporlife DCF) in sequence, first pre filters of 0.8 μm and 0.45 μm, respectively, then the final sterile filtration (0.22 μm), testing 836 ml of purified material for experiment A, with an initial protein concentration of 1.1 mg/ml, and IL for experiment B. The OMV protein concentrations after the filtration were 0.12 mg/ml and 0.59 mg/ml respectively.

OMVs were characterised as follows:

|  | Experiment A | Experiment B | Specification |
|---|---|---|---|
| Deoxycholate (μg/g protein) | 1.5 | 0.4 | 0.1-0.4 |
| DNA (μg/g protein) | 0.004 | 0.004 | <0.035 |
| Endotoxin (UI/g protein) | $2.8 \times 10^3$ | $2.6 \times 10^3$ | $<20 \times 10^3$ |
| LPS (μg/g protein) | 0.05 | 0.08 | 0.06-0.12 |
| SDS page |  |  |  |
| 80 kDa | 1.7 | 2.2 | 1-4 |
| 70 kDa | 11.8 | 12.7 | 1-12 |
| class I | 24.6 | 25.1 | 22-32 |
| class III | 34.8 | 32.8 | 30-43 |
| class IV | 12.0 | 12.2 | 9-18 |
| class V | 15.0 | 15.1 | 10-24 |

Thus the OMVs prepared using ultrafiltration have a similar composition to those obtained by ultracentrifugation. In comparison to the prior art method, however, the method of the invention is much simpler and quicker.

Example 2

OMVs from Meningococcal Serogroup B (New Zealand Strain)

*N. meningitidis* serogroup B (strain NZ 98/254, from New Zealand) was cultured as before, except that: (a) Catlin medium was used in place of Frantz' medium; (b) the initial 150 ml cultures were grown to a level ready for transferring into a Chemap fermentor with 300 L capacity, containing 120 L of pre-sterilized medium; (c) growth in the Chemap fermentor was for 12 hours; (d) growth was terminated at $OD_{590nm}$ of 5.90.

Transfer from the fermentor was as before, except that concentration was performed until 5 L volume.

Concentration was performed as before.

pH was adjusted as before, except that: (a) the final pH was 8.6; (b) the amount of 0.1 M Tris-HCl buffer added was 6 L.

Inactivation/extraction was as before, except: (a) 600 ml of the Tris-HCl buffer was added; (b) the volume of extracted suspension was 19.5 L.

Preparation of crude OMVs was as before, except: (a) centrifuge tubes were 1000 ml volume; (b) centrifugation was at 8000 rpm (16650×g), to give 17.5 L of supernatant.

Cross-flow filtration for purifying OMVs (in place of centrifugation) was as in experiment B above, except: (a) using 17.5 L crude OMVs; (b) using two P2B300V05 polyethersulphone filters (300 kD cutoff); (c) using an initial transfer of 4 L crude OMVs; (d) diafiltration with 30 L Tris-HCl buffer; (e) pellet was resuspended in 1.2 L of 3% sucrose; (f) the homogenous material was further sonicated, and gave a final concentration of purified material of 1.5 g/L total protein.

Final purification was as before, except: (a) filtration was through two capsule filters (Sartoclean CA, Sartobran P) in sequence, first pre-filters of 0.8+0.65 μm, then a final sterile filtration 0.45+0.22 μm. The OMV protein concentration after the filtration was 1.0 g/L.

OMVs were characterised as follows:

|  | Example 2 | Specification |
|---|---|---|
| Deoxycholate (μg/g protein) | 0.4 | 0.1-0.4 |
| DNA (μg/g protein) | 0.0005 | <0.035 |
| Endotoxin (UI/g protein) | 5393 | $<20 \times 10^3$ |
| LPS (μg/g protein) | 0.10 | 0.06-0.12 |
| SDS page |  |  |
| 80 kDa | 3.8 | 1-4 |
| 70 kDa | 6.4 | 1-12 |
| class I | 18.7 | 22-32 |
| class III + FbpA | 31.3 | 30-43 |
| class IV | 10.7 | 9-18 |
| class V | 2.7 | 10-24 |
| NspA | 3.9 | 1-7 |

Thus the production method provided OMVs with a native antigen mosaic and a strongly reduced level of LPS. In comparison to the prior art method where two ultracentrifugation steps are used, however, the invention is much simpler and quicker.

Example 3

OMVs from Meningococcal Serogroup B (New Zealand Strain)

Crude OMVs were prepared from the 98/254 strain as described above. The pH was adjusted to between 7.5 and 9.0 (typically between 8.3 and 8.5) with buffer, and then concentrated up to 20 liters by ultrafiltration for between 3.5 and 4.5 hours using Polysulphone Millipore Pellicon 2 cassettes with a surface area of 3 m². The concentrate material was diafiltered against 7 volumes of a solution containing Tris-EDTA, 1% DOC and 20% sucrose ('buffer B'), and then with 3 volumes of 'buffer B1' (same as 'buffer B' but with only 0.5% DOC). The retentate was concentrated again up to 4 liters and collected. The ultrafiltration system was washed with buffer B1. The retentate was then washed, and OMVs (retentate+washes) were stored at 2-8° C. The bioburden in the final material was zero, and endotoxin content was <0.05 UI/ml. The process showed excellent lot-to-lot consistency.

The stored material was centrifuged in a Beckman Coulter Optima XL 100K ultracentrifuge using a type 19 rotor and 250 ml Beckman bottles (220±10 ml material per bottle), 19000 rpm for 408 minutes at 2-8° C. Pellets were washed in 10 ml of a 3% sucrose solution, and were then re-suspended in 3% sucrose (60 ml volume added) using a 700 rpm magnetic agitator (2.5 cm bar) in 250 ml Beckman bottles. Re-suspended material was sonicated for 300 minutes at <20° C. If necessary, the sonicated material was diluted with 3% sucrose solution to give a final protein concentration of 1.2 mg/ml. The bioburden in the final material was zero, and the process showed excellent lot-to-lot consistency.

The OMVs were subjected to a final filtration step, first through 0.8-0.65 μm filters and then through 0.22 μm filters. The sonicated OMVs were passed into a sterile glass container with Sartoclean CA 0.8-0.65 μm 0.2 m² pre-filters. This pre-filtration was performed for 5-6 minutes with a peristaltic pump using only one set of filters. The filtrate was then passed into a second sterile glass container with Sartobran P 0.45-0.22 μm 0.4 m² filters. This filtration lasted 7-10 minutes, again with peristaltic pumps. The pre-filters were first rinsed with 500-600 ml of 3% sucrose, and the 0.22 μm filters were washed with 200 ml of 5% sucrose after filtration. Final OMV material was stored at 2-8° C., and contained <0.16 μg LPS per μg of protein and <0.4 kg DOC per μg of protein. Bioburden was zero. Protein content in the OMVs was between 800 μg/ml and 1000 μg/ml.

It will be understood that the invention has been described by way of example only and modifications may be made whilst remaining within the scope and spirit of the invention.

REFERENCES (THE CONTENTS OF WHICH ARE HEREBY INCORPORATED BY REFERENCE)

[1] Bjune et al. (1991) *Lancet* 338(8775):1093-1096.
[2] de Kleijn et al. (2001) *Vaccine* 20:352-358.
[3] U.S. Pat. No. 5,597,572.
[4] U.S. Pat. No. 5,747,653.
[5] European patent 0449958.
[6] European patent application 0680512.
[7] WO00/25811.
[8] WO01/52885.
[9] WO01/09350.
[10] WO02/09746.
[11] WO01/91788.
[12] Claassen et al. (1996) *Vaccine* 14:1001-1008.
[13] Cartwright et al. (1999) *Vaccine* 17:2612-2619.
[14] Peeters et al. (1996) *Vaccine* 14:1009-1015.
[15] Fu et al. (1995) *Biotechnology NY* 12:170-174.
[16] Fredriksen et al. pages 818-824 of *Pathobiology and immunobiology of Neisseriaceae* (eds. Conde-Glez et al.) ISBN 968-6502-13-0.
[17] Davies et al. (1990) *J. Immunol. Meth.* 134:215-225.
[18] Saunders et al. (1999) *Infect. Immun.* 67:113-119.
[19] Draabick et al. (2000) *Vaccine* 18:160-172.
[20] Moreno et al. (1985) *Infect. Immun.* 47:527-533.
[21] Milagres et al. (1994) *Infect. Immun.* 62:4419-4424.
[22] Naess et al. (1998) *Infect. Immun.* 66:959-965.
[23] Rosenqvist et al. (1998) *Dev. Biol. Stand* 92:323-333.
[24] Haneberg et al. (1998) *Infect. Immun.* 66:1334-1341.
[25] Andersen et al. (1997) *Vaccine* 15:1225-1234.
[26] European patent 0011243.
[27] Fredriksen et al. (1991) *NIPH Ann.* 14(2):67-80.
[28] WO2004/019977.

[29] U.S. Pat. Nos. 5,552,146, 5,981,213 & 5,993,826; see also WO93/03761.
[30] Zhou et al. (1998) *FEMS Microbiol Lett* 163:223-228.
[31] Kadurugamuwa & Beveridge (1999) *Microbiology* 145:2051-2060.
[32] WO97/05899.
[33] Blanco et al. (1999) *J Immunol* 163:2741-2746.
[34] Kesavalu et al. (1992) *Infect. Immun.* 60:1455-1464.
[35] Keenan et al. (1998) *FEMS Microbiol Lett* 161:21-27.
[36] WO00/50074.
[37] Parmar et al. (1997) *Vaccine* 15:1641-1651.
[38] WO99/59625.
[39] Maiden et al. (1998) *PNAS USA* 95:3140-3145.
[40] WO99/10497.
[41] WO02/07763.
[42] European patent 0624376.
[43] Adu-Bobie et al. (2004) *Infect Immun* 72:1914-1919.
[44] WO 02/062378.
[45] WO 2004/014417.
[46] Gennaro (2000) *Remington: The Science and Practice of Pharmacy.* 20th ed. ISBN: 0683306472.
[47] Bakke et al. (2001) *Infect. Immun.* 69:5010-5015.
[48] Katial et al. (2002) *Infect. Immun.* 70:702-707.
[49] *Vaccine design: the subunit and adjuvant approach,* eds. Powell & Newman, Plenum Press 1995 (ISBN 0-306-44867-X).
[50] WO90/14837.
[51] WO02/26212.
[52] WO98/33487.
[53] WO00/07621.
[54] WO99/27960.
[55] WO98/57659.
[56] European patent applications 0835318, 0735898 and 0761231.
[57] Krieg (2000) *Vaccine* 19:618-622; Krieg (2001) *Curr opin Mol Ther* 2001 3:15-24; WO96/02555, WO98/16247, WO98/18810, WO98/40100, WO98/55495, WO98/37919 and WO98/52581 etc.
[58] WO99/52549.
[59] WO01/21207.
[60] WO01/21152.
[61] WO00/62800.
[62] WO00/23105.
[63] WO99/11241.
[64] Del Giudice et al. (1998) *Molecular Aspects of Medicine,* vol. 19, number 1.
[65] Johnson et al. (1999) *Bioorg Med Chem Lett* 9:2273-2278.
[66] WO00/50078.
[67] Singh et al. (2001) *J. Cont. Rele.* 70:267-276.
[68] WO03/009869.
[69] Costantino et al. (1999) *Vaccine* 17:1251-1263.
[70] Covacci & Rappuoli (2000) *J. Exp. Med.* 19:587-592.
[71] WO93/18150.
[72] Covacci et al. (1993) *Proc. Natl. Acad. Sci. USA* 90:5791-5795.
[73] Tummuru et al. (1994) *Infect. Immun.* 61:1799-1809.
[74] Marchetti et al. (1998) *Vaccine* 16:33-37.
[75] Telford et al. (1994) *J. Exp. Med.* 179:1653-1658.
[76] Evans et al. (1995) *Gene* 153:123-127.
[77] WO96/01272 & WO96/01273, especially SEQ ID NO:6.
[78] WO97/25429.
[79] WO98/04702.
[80] Watson (2000) *Pediatr Infect Dis J* 19:331-332.
[81] Rubin (2000) *Pediatr Clin North Am* 47:269-285, v.
[82] Jedrzejas (2001) *Microbiol Mol Biol Rev* 65:187-207.
[83] Bell (2000) *Pediatr Infect Dis J* 19:1187-1188.
[84] Iwarson (1995) *APMIS* 103:321-326.
[85] Gerlich et al. (1990) *Vaccine* 8 Suppl:S63-68 & 79-80.
[86] Hsu et al. (1999) *Clin Liver Dis* 3:901-915.
[87] *Vaccines* (1988) eds. Plotkcin & Mortimer. ISBN 0-7216-1946-0.
[88] Gustafsson et al. (1996) *N. Engl. J. Med.* 334:349-355.
[89] Rappuoli et al. (1991) *TIBTECH* 9:232-238.
[90] Sutter et al. (2000) *Pediatr Clin North Am* 47:287-308.
[91] Zimmerman & Spann (1999) *Am Fam Physician* 59:113-118, 125-126.
[92] WO99/24578.
[93] WO99/36544.
[94] WO99/57280.
[95] WO02/079243.
[96] WO02/02606.
[97] Kalman et al. (1999) *Nature Genetics* 21:385-389.
[98] Read et al. (2000) *Nucleic Acids Res* 28:1397-406.
[99] Shirai et al. (2000) *J. Infect. Dis.* 181 (Suppl 3):S524-S527.
[100] WO99/27105.
[101] WO00/27994.
[102] WO00/37494.
[103] Ross et al. (2001) *Vaccine* 19:4135-4142.
[104] Dreesen (1997) *Vaccine* 15 Suppl:S2-6.
[105] *MMWR Morb Mortal Wkly Rep* 1998 Jan. 16; 47(1): 12, 19.
[106] Anderson (2000) *Vaccine* 19 Suppl 1:S59-65.
[107] Kahn (2000) *Curr Opin Pediatr* 12:257-262.
[108] Crowe (1995) *Vaccine* 13:415-421.
[109] McMichael (2000) *Vaccine* 19 Suppl 1:S10-107.
[1110] WO02/34771.
[111] Dale (1999) *Infect Dis Clin North Am* 13:227-43, viii.
[112] Ferretti et al. (2001) *PNAS USA* 98: 4658-4663.
[113] Kuroda et al. (2001) *Lancet* 357(9264):1225-1240; see also pages 1218-1219.
[114] *J Toxicol Clin Toxicol* (2001) 39:85-100.
[115] Demicheli et al. (1998) *Vaccine* 16:880-884.
[116] Stepanov et al. (1996) *J Biotechnol* 44:155-160.
[117] Ingram (2001) *Trends Neurosci* 24:305-307.
[118] Rosenberg (2001) *Nature* 411:380-384.
[119] Moingeon (2001) *Vaccine* 19:1305-1326.
[120] Ramsay et al. (2001) *Lancet* 357(9251):195-196.
[121] Lindberg (1999) *Vaccine* 17 Suppl 2:S28-36.
[122] Buttery & Moxon (2000) *J R Coll Physicians Lond* 34:163-168.
[123] Ahmad & Chapnick (1999) *Infect Dis Clin North Am* 13:113-133, vii.
[124] Goldblatt (1998) *J. Med. Microbiol.* 47:563-567.
[125] European patent 0 477 508.
[126] U.S. Pat. No. 5,306,492.
[127] WO98/42721.
[128] *Conjugate Vaccines* (eds. Cruse et al.) ISBN 3805549326, particularly vol. 10:48-114.
[129] Hermanson (1996) *Bioconjugate Techniques* ISBN: 0123423368 or 012342335X.
[130] *Research Disclosure,* 453077 (January 2002)
[131] EP-A-0372501
[132] EP-A-0378881
[133] EP-A-0427347
[134] WO93/17712
[135] WO94/03208
[136] WO98/58668
[137] EP-A-0471177
[138] WO00/56360
[139] WO91/01146
[140] WO00/61761

[141] WO01/72337
[142] Costantino et al. (1992) *Vaccine* 10:691-8.
[143] Lieberman et al. (1996) *JAMA* 275:1499-503.
[144] WO02/058737.
[145] WO02/00249.
[146] WO03/007985.
[147] Rennels et al. (2002) *Pediatr Infect Dis J* 21:978-979.
[148] Campbell et al. (2002) *J Infect Dis* 186:1848-1851.
[149] Robinson & Torres (1997) *Seminars in Immunology* 9:271-283.
[150] Donnelly et al. (1997) *Annu Rev Immunol* 15:617-648.
[151] Scott-Taylor & Dalgleish (2000) *Expert Opin Investig Drugs* 9:471-480.
[152] Apostolopoulos & Plebanski (2000) *Curr Opin Mol Ther* 2:441-447.
[153] Ilan (1999) *Curr Opin Mol Ther* 1:116-120.
[154] Dubensky et al. (2000) *Mol Med* 6:723-732.
[155] Robinson & Pertmer (2000) *Adv Virus Res* 55:1-74.
[156] Donnelly et al. (2000) *Am J Respir Crit Care Med* 162(4 Pt 2):S190-193.
[157] Davis (1999) *Mt. Sinai J. Med* 66:84-90.
[158] WO02/09643.
[159] U.S. Pat. No. 6,180,111.
[160] WO01/34642.

The invention claimed is:

1. A process for preparing bacterial outer membrane vesicles (OMVs), comprising
    (a) applying ultrafiltration to crude OMVs to produce a retentate with the OMVs;
    (b) applying ultracentrifugation to the OMVs in the retentate to produce a pellet with the OMVs; and
    (c) resuspending the OMVs from the pellet.

2. The process of claim 1, wherein the crude OMVs are an aqueous suspension of OMVs that have been prepared from bacteria.

3. The process of claim 1, wherein the ultrafiltration step results in diafiltration.

4. The process of claim 1, wherein the ultrafiltration is cross-flow or tangential flow.

5. The process of claim 1, wherein the membrane used for ultrafiltration has a cut-off of about 300 kDa.

6. The process of claim 1, wherein the OMVs are sterilised after ultrafiltration.

7. The process of claim 6, wherein the sterilisation is by filter sterilisation.

8. A process for preparing bacterial OMVs, comprising the steps of: (a) cultivating bacterial cells; (b) collecting and/or concentrating the cultivated cells; (c) disrupting the outer membranes of the cultivated cells; and (d) preparing OMVs by the method of claim 1.

9. The process of claim 1, further comprising the step of combining the OMVs with a pharmaceutical carrier and/or adjuvants and/or stabiliser.

10. The process of claim 1, wherein the bacterium for OMV preparation is Gram negative.

11. The process of claim 10, wherein the bacterium is *Neisseria meningitidis*.

12. The process of claim 11, wherein the bacterium is serogroup B *N. meningitidis*.

13. The process of claim 12, wherein the bacterium is a B:4:P1.4 strain, a B:4:P1.15 strain, a B:4:P1.19,15 strain, a B:4:P1.7b,4 strain or a B:15:P1.7,16 strain.

14. The process of claim 11, wherein the *N. meningitidis* has one or more mutations to decrease or knockout expression of a gene product.

15. The process of claim 14, wherein the gene product is Cps, CtrA, CtrB, CtrC, CtrD, ExbB, ExbD, FrpB, GalE, HtrB, MsbB, LbpA, LbpB, LpxK, NMB0033, OpA, OpC, PhoP, PilC, PmrE, PmrF, PorA, PorB, rmpM, SiaA, SiaB, SiaC, SiaD, SynA, SynB, SynC, TbpA and/or TbpB.

* * * * *